US008140456B2

(12) United States Patent
Hamamoto et al.

(10) Patent No.: US 8,140,456 B2
(45) Date of Patent: Mar. 20, 2012

(54) METHOD AND SYSTEM OF EXTRACTING FACTORS USING GENERALIZED FISHER RATIOS

(75) Inventors: Yoshihiko Hamamoto, Ube (JP); Masaaki Oka, Ube (JP)

(73) Assignee: Yamaguchi University, Yamaguchi (JP)

( * ) Notice: Subject to any disclaimer, the term of this patent is extended or adjusted under 35 U.S.C. 154(b) by 210 days.

(21) Appl. No.: 12/156,094

(22) Filed: May 29, 2008

(65) Prior Publication Data

US 2008/0319711 A1 Dec. 25, 2008

Related U.S. Application Data

(63) Continuation of application No. PCT/JP2006/324019, filed on Nov. 30, 2006.

(30) Foreign Application Priority Data

Dec. 2, 2005 (JP) .................................. 2005-349541

(51) Int. Cl.
*G06F 17/15* (2006.01)
(52) U.S. Cl. .......................................... 706/46; 702/19
(58) Field of Classification Search ........................ None
See application file for complete search history.

(56) References Cited

U.S. PATENT DOCUMENTS

| 6,647,341 | B1 * | 11/2003 | Golub et al. .................... 702/19 |
| 2005/0159896 | A1 | 7/2005 | Ishikawa et al. |
| 2005/0262031 | A1 * | 11/2005 | Saidi et al. ...................... 706/21 |

FOREIGN PATENT DOCUMENTS

| JP | 2003-61678 | 3/2003 |
| JP | 2004-298178 | 10/2004 |
| JP | 2005-38256 | 2/2005 |

OTHER PUBLICATIONS

Golub TR, Slonim DK, Tamayo P, et al; "Molecular Classification of Cancer: Class Discovery and Class Prediction by Gene Expression Monitoring"; Science vol. 286; Oct. 13, 1999; pp. 531-537.*
Guyon I, Elisseeff A; "An Introduction to Variable and Feature Selection"; J Mach Learn Res vol. 3; 2003; pp. 1157-1182.*
Xiong M, Li W, Zhao J, Jin L, Boerwinkle E; "Feature (Gene) Selection in Gene Expression-Based Tumor Classification"; Mol Genet Metabol vol. 73; 2001; 239-247.*
Bi J, Bennett K, Embrechts M, Breneman CM, Song M; "Dimensionality Reduction via Sparse Support Vector Machines"; J Mach Learn Res vol. 3; 2003; pp. 1229-1243.*

(Continued)

*Primary Examiner* — Marjorie Moran
*Assistant Examiner* — Soren Harward
(74) *Attorney, Agent, or Firm* — Muramatsu & Associates

(57) ABSTRACT

To provide an effective factor extraction system in which samples are generated artificially from a sample group and a virtual sample set is created so that even when the number of sample is relatively small, specific factors can be selected/extracted with high reliability by using the virtual sample set. The effective factor extraction system comprises a section for extracting samples arbitrarily from sample sets and creating a plurality of paired virtual sample sets, a statistical quantity operating section for reading out the feature value held by sample contained in respective virtual sample sets and operating the average value and the variance, a section for operating Fisher ratio from the average value and the variance, and a section for testing significant factors using the operated Fisher ratio.

6 Claims, 11 Drawing Sheets

OTHER PUBLICATIONS

Ambroise C, McLachlan GJ; "Selection bias in gene extraction of the basis of microarrach gene-expression data"; Proc Natl Acad Sci vol. 99 nr 10; May 14, 2002; pp. 6562-6566.*

Dash M, Lin H; "Feature Selection for Classification"; Intell Data Anal vol. 1; 1997; pp. 131-156.*

Furey TS, Cristianini N, Duffy N, et al; "Support vector machine classification and validation of cancer tissue samples using microarray expression data"; Bioinform vol. 16 nr 10; 2000; pp. 906-914.*

Guyon I, Weston J, Barnhill S, Vapnik V; "Gene Selection for Cancer Classification using Support Vector Machines"; Mach Learn vol. 46; 2002; pp. 389-422.*

Xing EP, Jordan MI, Karp RM; "Feature selection for high-dimensional genomic microarray data"; Proc 18th Intl Conf Mach Learn; 2001; pp. 601-608.*

Liu, B., Cui, Q., Jiang, T. & Ma, S. A combinational feature selection and ensemble neural network method for classification of gene expression data. BMC Bioinformatics 5, 136-1-136-12 (2004).*

"Oligonucleotide microarray for prediction of early intrahepatic recurrence of hepatocelluar carcinoma after curative resection" The Lancet, vol. 361, Mar. 15, 2003.

"Kanzo ni okeru genomics kenkyu; 7. Kansaibogan Ten'i yosoku", Japan Society of Hepatology, vol. 46, No. 10, Oct. 25, 2005.

* cited by examiner

FIG. 10

| Patient No. \ Gene No. | Virtual sample set (Recurrence group) | | | Virtual sample set $Y^t$ (Non-recurrence group) | | |
|---|---|---|---|---|---|---|
| | Patient $x_1$ | Patient $x_2$ | Patient $x_3$ | Patient $y_1$ | Patient $y_2$ | Patient $y_3$ |
| $g_1$ | 5157 | 9863 | 4091 | 2010 | 2957 | 3818 |
| $g_2$ | 74 | 133 | 198 | 332 | 350 | 465 |
| $g_3$ | 702 | 1412 | 2138 | 3561 | 4283 | 3535 |
| $g_4$ | 134 | 10 | 74 | 125 | 446 | 258 |
| $g_5$ | 1474 | 528 | 1628 | 850 | 5772 | 3393 |

FIG. 11

| Gene No. | Virtual sample set $X^t$ (Recurrence group) | | Virtual sample set $Y^t$ (Non-recurrence group) | | Fisher ratio |
|---|---|---|---|---|---|
| | Average $\mu_1$ | Variance $\sigma_1^2$ | Average $\mu_2$ | Variance $\sigma_2^2$ | |
| $g_1$ | 6370.3 | 9433129.3 | 2928.3 | 817832.3 | 2.31 |
| $g_2$ | 135.0 | 3847.0 | 382.3 | 5206.3 | 13.51 |
| $g_3$ | 1417.3 | 515545.3 | 3793.0 | 180244.0 | 16.22 |
| $g_4$ | 72.7 | 3845.3 | 276.3 | 26012.3 | 2.78 |
| $g_5$ | 1210.0 | 354772.0 | 3338.3 | 6058762.3 | 1.41 |

METHOD AND SYSTEM OF EXTRACTING FACTORS USING GENERALIZED FISHER RATIOS

This application is a continuation of International Application No. PCT/JP2006/324019, filed 30 Nov. 2006, which in turn claims the benefit of Japanese Application No. 2005-349541, filed on 2 Dec. 2005.

FIELD OF THE INVENTION

The present invention relates to an effective factor extraction system and its method and program for extracting effective factors that are considered as appropriate targets for discriminating between two groups based on the sample sets having a quantitative feature value with respect to each factor.

BACKGROUND OF THE INVENTION

In general, an operation in which samples are arbitrarily extracted and analyzed from a sample set that includes specific factors, and the effective factors are then selected for an intended determination or identification, has been implemented in various industrial fields.

Especially, such a technology of selecting effective factors is researched with respect to micro-array technology that has rapidly progressed recently and bio-informatics that apply the micro-array technology. Namely, when a gene is considered as a factor, for example, and in order to select the genes that may be related to cancer, the sample sets from cancer and non-cancer patients are analyzed, and the genes that are highly likely to be related to carcinogenesis are selected.

The micro-array technology is rapidly progressing by application of the nanotechnology, where the genes can be analyzed comprehensively and systematically based on their gene expressions. The micro-array quantifies mRNA in a biological system, thereby enabling to measure all the expressed amounts of the respective genes. How to achieve useful knowledge from an extensive amount of gene expression information provided from the micro-arrays depend entirely on the bio-informatics, thus, the bio-informatics play an extremely important role in the field of life science.

The micro-array technology and the bio-informatics have a close relationship with one another where they both need to progress hand in hand, otherwise no meaning/value will be found. The micro-array technology in Japan is ranked highest among the world, yet on the other hand, currently, the bio-informatics has greatly fallen behind other countries, thus, the micro-array research lacks in international competitive strength contrary to the high level of its technology.

Therefore, an immediate advancement in research and development is desired in the bio-informatics. Currently, there are several technologies related to this field that have been proposed.

For example, patent document 1, Japanese Laid-Open Publication No. 2005-38256, discloses an invention by the title of "Effective Factor Information Selection Apparatus, Effective Factor Information Selection Method, Program, and Recording Medium", where a factor effective for multivariate analysis and pattern recognition is selected, thereby effectively reducing the number of factors.

In the effective factor information selection apparatus disclosed by this document, in order to select the factors that are effective in the multivariate analysis by using samples, an average and a standard deviation are determined from two groups of sample information with different attributes, where more specifically, they utilize the equations shown in the specification of this document.

According to this effective factor information selection apparatus, when there are two groups, by selecting the effective factors that show differences between the two groups, the effective factor information can be selected.

Further, patent document 2, Japanese Laid-Open Publication No. 2003-61678, discloses an invention by the title of "Screening Method and Sensitivity Determining Method of Genes" where although it is an invention specified for screening the genes, it is also a method that enables to select and extract a gene associated with sensitivity to medication and radiation.

The method disclosed by this document includes a process for dividing several disease carrying patients into a first patient group who show signs of sensitivity to medication or radiation and a second patient group who show no signs of sensitivity to medication or radiation, a process for analyzing the expression profiles of the genes from the first patient group and the second patient group, and a process for selecting one or more genes that show a significantly different degree of expression by statistically examining the genes between the first and second patient groups.

Further, patent document 3, Japanese Laid-Open Publication No. 2004-298178, discloses an invention by the title of "Statistical Analysis of Adjusting Factor Bond Part of Differentially Expressed Gene" where the adjusting factor bond parts with differentially expressed gene are identified and characterized.

The technology disclosed by this document is systematic analysis of the adjusting factor bond part of the differentially expressed gene which is a statistical analysis method of the differentially expressed gene. The analysis method includes a process for obtaining a set of differentially expressed genes, a process for screening a genome arrangement including an adjustment range of the differentially expressed genes in the existence of the adjusting factor bond part, and a process for comparing it either with a background of the genome scale or a background of the system scale and identify at least one of the adjusting factor bond parts enriched within the set of the differentially expressed genes.

DISCLOSURE OF THE INVENTION

Problems to be Solved by the Invention

In the conventional technologies described in the patent documents 1-3 noted above, a factor that has the specific information from the sample group is selected and extracted by applying a statistical process for the factors such as genes.

However, in these conventional technologies, when the number of available samples is relatively small, it is not shown how the selection and extraction of the factors influence the accuracy or what kind of measure should be taken in order to improve the accuracy.

In these conventional technologies, the extraction of factors existing within the sample group is executed with use of statistical means when evaluating their significance, however, the influence of the number of samples that is thought to largely affect the significance in that procedure is not taken into consideration.

When the number of samples is sufficient, a highly accurate processing can be done by taking a sufficient analysis time depending on the number of samples. However, when considering the factor as a gene, for example, as well as attributes such as cancer and non-cancer as specific information, the information related to the cancer patients that can be obtained as samples is limited physically and due to privacy issues, and since cancer has various aspects, it is extremely difficult to secure a sufficient number of samples for conducting such analysis. Thus, there is a serious problem in that when using the method and apparatus in the conventional technology, the accuracy or precision as to whether the extracted factor incorporates a specific attribute and information is not high enough.

Therefore, the present invention has been made in consideration of the conventional situations noted above, and it is an object of the present invention to provide an effective factor extraction system and its method and program that are capable of selecting/extracting target factors with high reliability by using virtual sample sets created by artificially generating the virtual samples from available samples even when the number of samples is relatively small.

Means to Solve the Problems

In order to achieve the above object, the first aspect of the present invention is an effective factor extraction system which is comprised of a virtual sample set creating section (3) for arbitrarily extracting samples from each sample set (15, 16) and creating repeatedly paired virtual sample sets (17, 18) where each of the samples have a quantitative feature value in their factors; a statistical quantity operating section (5) for reading out the feature values contained in all of virtual samples in each virtual sample set (17, 18) and calculating an average value (21) and a variance value (22) thereof; a statistical distance operating section (6) for calculating a statistical distance (23) between the groups based on the average value and the variance value of each group with respect to each of the factors; and a testing section (8) for testing the factors that are significant to distinguish two groups with use of the statistical distance (23) calculated for each of the factors.

The above mentioned effective factor extraction system is so structured to achieve a function for calculating the average value and the variance value for each of the factors in the feature value reserved by the virtual sample sets created by the virtual sample set creating section. Further, it is also structured to achieve a function for calculating the statistical distance among the groups based on the average values and the variance values, and for testing the significant factors based on the statistical distance.

Further, in the second aspect of the present invention, the effective factor extraction system of the first aspect further includes a frequency analyzing section for reading out the significant factors tested by the testing section (8) for each of the virtual sample sets (17, 18) and extracting the factors existing with a frequency higher than a predetermined frequency for all of the virtual sample sets (17, 18).

This effective factor extraction system is structured to achieve a function for extracting the significant factors based on the predetermined frequency as a threshold value from the significant factors that have been retrieved.

Further, the third aspect of the present invention is an effective factor extraction system which is comprised of a virtual sample set creating section (3) for arbitrarily extracting samples from each sample set (15,16) and creating repeatedly paired virtual sample sets (17, 18) where each of the samples have a quantitative feature value in their factors; a statistical quantity operating section (5) for reading out the feature values contained in all of virtual samples that belong to each of the virtual sample sets (17, 18) with respect to each of the factors and calculating an average value (21) and a variance value (22) thereof; a statistical distance operating section (6) for calculating a statistical distance (23) between the groups based on the average value (21) and the variance value (22) of each group with respect to each of the factors; a testing section (8) for testing the factors that are significant to distinguish two groups with use of the statistical distance (23) calculated for each of the factors; a frequency analyzing (9) section for reading out the significant factors tested in the testing section (8) for each of the virtual sample sets (17, 18) and extracting the factors existing with a frequency higher than a predetermined frequency for all of the virtual sample sets (17, 18); and a generalized statistical distance operating section (10) for calculating a generalized statistical distance (24) from the average values and the variance values of all of the statistical distances (23) of the virtual sample sets with respect to each of the factors extracted by the frequency analyzing section (9).

This effective factor extraction system is structured to achieve, in addition to the function of the second aspect noted above, a function for calculating the statistical distances of all of the paired virtual sample sets with respect to each of the factors extracted by the frequency analyzing section.

Further, the effective factor extraction system in the fourth aspect of the present invention includes, in addition to the effective factor extraction system in the first to third aspects noted above, a sorting section (7) for rearranging factors by using the statistical distances (23, 24) calculated by the statistical distance operating section (6) or the generalized statistical distance operating section (10) as a key.

The effective factor extraction system is structured to achieve, in addition to the function of the invention in the first to third aspects noted above, a function for rearranging the factors based on the statistical distance as the key.

In the effective factor extraction system in the fifth aspect of the present invention, in addition to the effective factor extraction system in the first to third aspects noted above, the factor is a gene, and the quantitative parameter amount is an mRNA.

The function of the above effective factor extraction system is similar to the functions of the inventions in the first to fourth aspects noted above.

The sixth aspect of the present invention is an effective factor extraction method which is comprised of a virtual sample set creating process for arbitrarily extracting samples from each sample set (15,16) and creating repeatedly paired virtual sample sets (17, 18) where each of the samples have a quantitative feature value in their factors; a statistical quantity operating process for reading out the feature values contained in all of virtual samples in each group that belongs to each of the virtual sample sets (17, 18) with respect to each of the factors and calculating an average value (21) and a variance value (22) thereof; a statistical distance operating process for calculating a statistical distance (23) between the groups based on the average value and the variance value of each group with respect to each of the factors; and a testing process for testing the factors that are significant to distinguish two groups with use of the statistical distance (23) calculated for each of the factors.

In the above effective factor extraction method, the invention of the system in the first aspect noted above is redefined as a method invention, and the function thereof is similar to that of the first aspect.

The seventh aspect of the present invention is an effective factor extraction method which is comprised of a virtual sample set creating process for arbitrarily extracting samples from each sample set (15,16) and creating repeatedly paired virtual sample sets (17, 18) where each of the samples have a quantitative feature value in their factors; a statistical quantity operating process for reading out the feature values contained in all of virtual samples in each group that belongs to each of the virtual sample sets (17, 18) with respect to each of the factors and calculating an average value (21) and a variance value (22) thereof; a statistical distance operating process for calculating a statistical distance (23) between the groups based on the average value (21) and the variance value (22) of each group with respect to each of the factors; a testing process (8) for testing the factors that are significant to distinguish two groups with use of the statistical distance (23) calculated for each of the factors; a frequency analyzing process for reading out the significant factors tested in said testing process for each of the virtual sample sets (17, 18) and extracting the factors existing with a frequency higher than a predetermined frequency for all of the virtual sample sets (17, 18); and a generalized statistical distance operating process (10) for calculating a generalized statistical distance (24) from the average values and the variance values of all of the statistical distances (23) of the virtual sample sets with respect to each of the factors extracted by the frequency analyzing process.

In the above effective factor extraction method, the invention of the system in the third aspect noted above is redefined as a method invention, and the function thereof is similar to that of the third aspect.

The eighth aspect of the present invention is an effective factor extraction program which is comprised of a virtual sample set creating process for arbitrarily extracting samples from each sample set (15,16) and creating repeatedly paired virtual sample sets (17, 18) where each of the samples have a quantitative feature value in their factors; a statistical quantity operating process for reading out the feature values contained in all of virtual samples in each group that belongs to each of the virtual sample sets (17, 18) with respect to each of the factors and calculating an average value (21) and a variance value (22) thereof; a statistical distance operating process for calculating a statistical distance (23) between the groups based on the average value and the variance value of each group with respect to each of the factors; and a testing process for testing the factors that are significant to distinguish two groups with use of the statistical distance (23) calculated for each of the factors.

In the above effective factor extraction program, the invention of the system in the first aspect noted above is redefined as a software invention, and the function thereof is similar to that of the first aspect.

The ninth aspect of the present invention is an effective factor extraction program which is comprised of a virtual sample set creating process for arbitrarily extracting samples from each sample set (15,16) and creating repeatedly paired virtual sample sets (17, 18) where each of the samples have a quantitative feature value in their factors; a statistical quantity operating process for reading out the feature values contained in all of virtual samples in each group that belongs to each of the virtual sample sets (17, 18) with respect to each of the factors and calculating an average value (21) and a variance value (22) thereof; a statistical distance operating process for calculating a statistical distance (23) between the groups based on the average value (21) and the variance value (22) of each group with respect to each of the factors; a testing process (8) for testing the factors that are significant to distinguish two groups with use of the statistical distance (23) calculated for each of the factors; a frequency analyzing process for reading out the significant factors tested in said testing process for each of the virtual sample sets (17, 18) and extracting the factors existing with a frequency higher than a predetermined frequency for all of the virtual sample sets (17, 18); and a generalized statistical distance operating process (10) for calculating a generalized statistical distance (24) from the average values and the variance values of all of the statistical distances (23) of the virtual sample sets with respect to each of the factors extracted by the frequency analyzing process.

In the above effective factor extraction program, the invention of the system in the third aspect noted above is redefined as a software invention, and the function thereof is similar to that of the third aspect.

Effects of the Invention

In the effective factor extraction system of the present invention in the first to fifth aspects noted above, since the virtual sample set creating section arbitrarily extracts samples from the sample sets that have been divided into two groups by the arbitrarily predetermined attributes and creates repeatedly paired virtual sample sets, it is possible to perform the analysis for determining the statistical distance between the groups based on the average value data and variance value data of the feature values of the respective factors from the plurality of virtual sample sets. Thus, even when the number of samples is relatively small, the precision of analysis related to the factors can be improved. Further, since the testing section is provided so that it is possible to select the significant factors that can effectively distinguish two groups, the reliability of the factor extraction can be improved.

Similarly, in the effective factor extraction method of the present invention in the sixth and seventh aspects noted above, or in the effective factor extraction program of the present invention in the eighth and ninth aspects noted above, since the virtual sample set creating section arbitrarily extracts samples from the sample sets that have been divided into two groups by the arbitrarily predetermined attributes and creates repeatedly paired virtual sample sets, it is possible to perform the analysis for determining the statistical distance between the groups based on the average value data and variance value data of the feature values of the respective factors from the virtual sample sets. Thus, even when the number of samples is relatively small, the precision of analysis related to the factors can be improved. Further, since the testing section is provided so that it is possible to select the significant factors that can effectively distinguish two groups, the reliability of the factor extraction can be improved.

Especially, in the effective factor extraction system in the third aspect of the present invention noted above, since the generalized statistical distance is calculated based on the average value and variance value of the statistical distances of all of the virtual sample sets for the factors that have been once screened by the frequency analyzing process, a significant factor can be selected and extracted with even higher precision.

Further, in the effective factor extraction method in the seventh aspect of the present invention noted above or the effective factor extraction program in the ninth aspect of the present invention noted above, since the generalized statistical distance is calculated based on the average value and variance value of the statistical distances of all of the virtual sample sets for the factors that have been once screened by the frequency analyzing process, significant factors can be selected and extracted with even higher precision.

Especially, in the effective factor extraction system in the fourth aspect of the present invention noted above, since the factors can be rearranged according to the degree of the statistical distances, the significance can be easily determined.

BRIEF DESCRIPTION OF THE DRAWINGS

FIG. 10 is a table showing an example of creating virtual sample sets from sample sets of opposing groups such as a recurrence group and a non-recurrence group by using the virtual sample set creating section, and selecting a virtual sample set $X^t$ (recurrence group) and a virtual sample set $Y^t$ (non-recurrence group) from the created virtual sample sets.

FIG. 11 is a table showing the results of the Fisher ratio calculated from each of the virtual sample sets by using the data in FIG. 10.

REFERENCE NUMERALS

Figure 1:
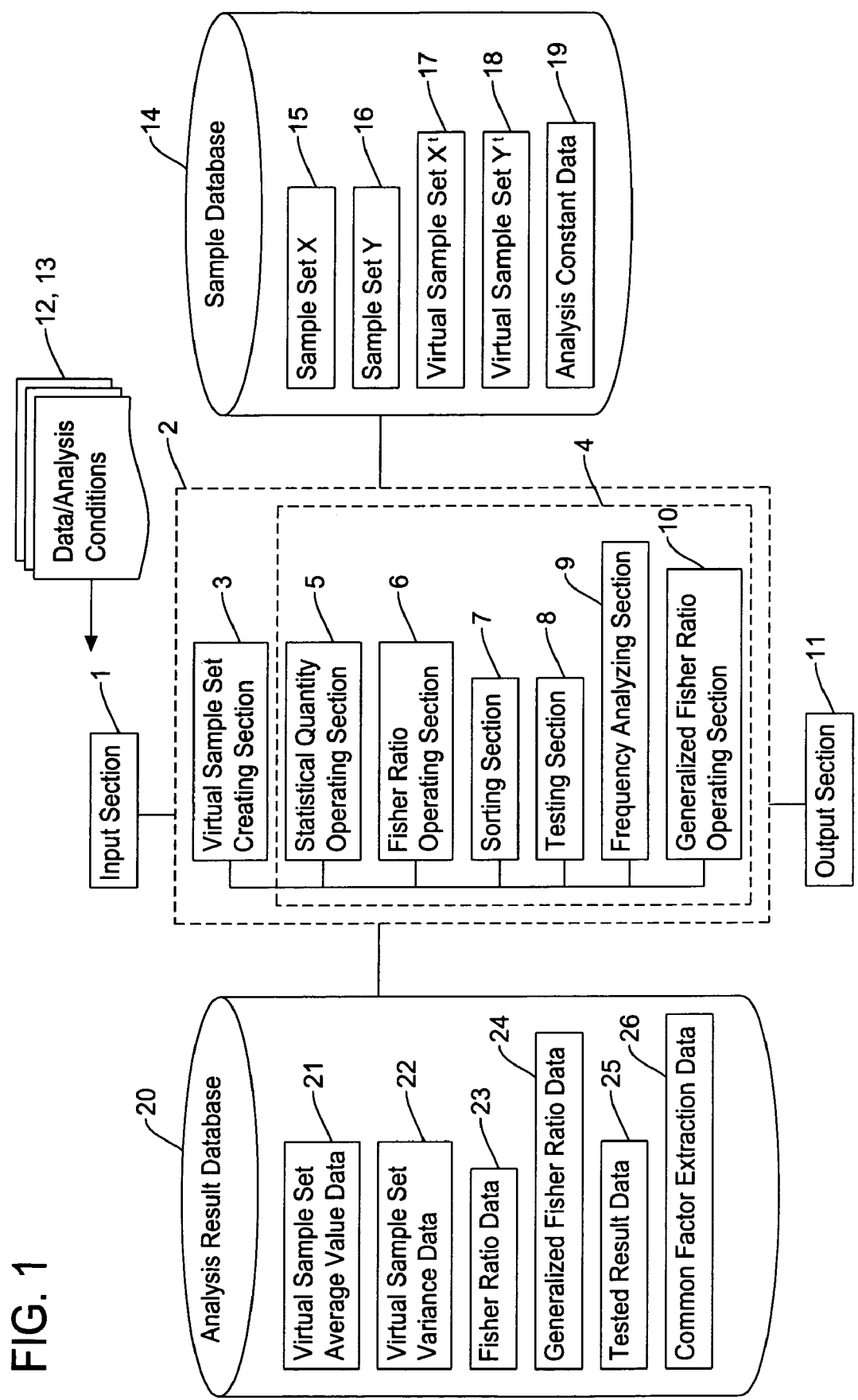
FIG. 1 is a schematic diagram showing the effective factor extraction system related to an embodiment of the present invention.

1 Input section
2 Operating section
3 Virtual sample set creating section
4 Factor selecting section
5 Statistical quantity operating section
6 Fisher ratio operating section
7 Sorting section
8 Testing section
9 Frequency analyzing section
10 Generalized Fisher ratio operating section
11 Output section
12 Data
13 Analysis conditions
14 Sample database
15 Sample set X
16 Sample set Y
17 Virtual sample set $X^t$
18 Virtual sample set $Y^t$
19 Sample set constant data
20 Analysis result database
21 Virtual sample set average value data
22 Virtual sample set variance value data
23 Fisher ratio data
24 Generalized Fisher ratio data
25 Tested result data
26 Factor extraction data

BEST MODE FOR IMPLEMENTING THE INVENTION

The effective factor extraction system, the effective factor extraction method, and the effective factor extraction program related to the preferred embodiment of the present invention will be explained below with reference to FIGS. 1~9. In the present embodiment, the Fisher ratio is used as a statistical distance between the distribution of the two groups, however, statistical distances other than the Fisher ratio such as a Chernoff distance, a Bhattacharyya distance, and Divergence can also be used. As the statistical distance between the distribution of the two groups, the Fisher ratio, Chernoff distance, Bhattacharyya distance, and Divergence are all calculated based on the average value data and variance value data of the distribution of the two groups to show the distance between the two groups, which indicates that the larger the distance, the larger the difference with respect to attributes between the two groups.

FIG. 1 is a structural diagram of the effective factor extraction system related to the embodiment of the present invention. In FIG. 1, the effective factor extraction system is comprised of an input section 1, an operating section 2, an output section 11, and two databases which are a sample database 14 and an analysis result database 20. In addition, the operating section 2 is comprised of a virtual sample set creating section 3 and a factor selecting section 4.

Regarding the effective factor extraction system related to the present embodiment, an example of system by which target genes such as cancer related genes are selected using the gene expression information from micro-arrays will be explained.

Figure 2:
FIG. 2 is a flow chart showing the operational flow of gene analysis using the effective factor extraction system related to the present embodiment.

In such a case, as shown in FIG. 2, the system extracts genes that are the target with use of the gene expression data retrieved from biological systems through micro-arrays under a series of flow which is a function of the analyzing section therein.

Figure 3:
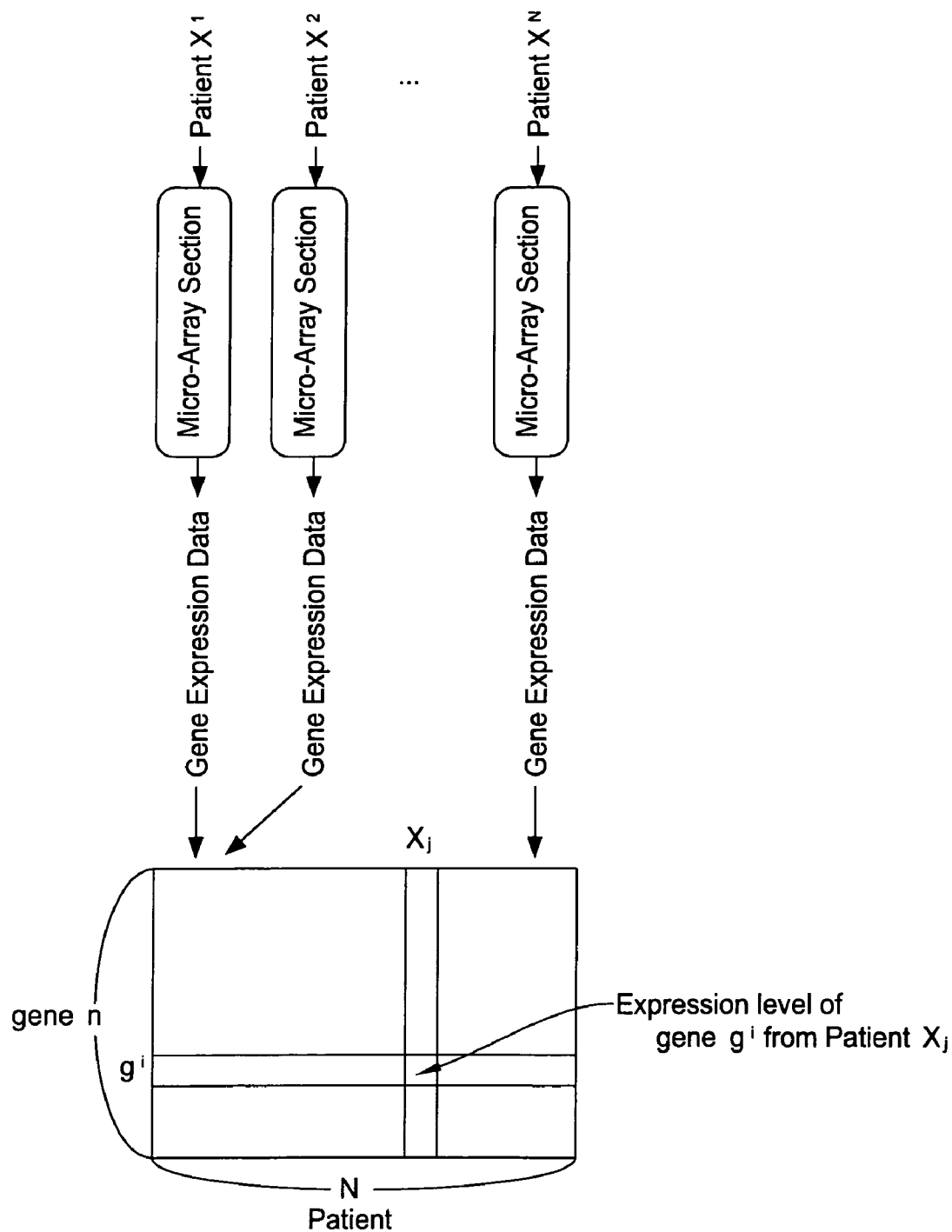
FIG. 3 is a schematic diagram for explaining the gene expression data.

Further, the gene expression data in FIG. 2 is interpreted as a set of the expression level (specifically, an mRNA amount) of the gene $g_i$ (i=1~n) of a patient $x_j$ (j=1~N) retrieved through the micro-arrays, as shown in more specifically in FIG. 3.

Referring back to FIG. 1, the input section 1 of the effective factor extraction system inputs a sample set X15 and a sample set Y16 stored in the sample database 14 or analysis conditions 13 for conducting a statistical analysis executed in the factor selecting section 4. The sample set X15 corresponds to the set of gene expression data shown in FIGS. 2 and 3. The sample set Y16 shown in FIG. 1 is a separate group provided with attributes that are different from that of the sample set X15.

The sample set X15 and the sample set Y16 are then stored in the sample database 14, and read out by the virtual sample set creating section 3 to produce a virtual sample set $X^r$17 and a virtual sample set $Y^r$18. It is also possible that the virtual sample set creating section 3 directly retrieves the sample set X15 and the sample set Y16 provided to the input section 1 to create the virtual sample sets.

Using this virtual sample set $X^r$17 and the virtual sample set $Y^r$18, the analysis is executed in the factor selecting section 4 to obtain the set of target genes. The factor selecting section 4 is comprised of a statistical quantity operating section 5, a Fisher ratio operating section 6, a sorting section 7, a testing section 8, a frequency analyzing section 9, and a generalized Fisher ratio operating section 10. The data related to the analysis results obtained by the analysis in the factor selecting section 4 is stored in the analysis result database 20 as a virtual sample set average value data 21, a virtual sample set variance value data 22, Fisher ratio data 23, and generalized Fisher ratio data 24, respectively.

The two sample sets X15 and Y16 are sets of samples respectively taken from two opposing groups, for example, in the case of cancer treatment at a medical facility, two groups representing, for example, "recurrence group vs. non-recurrence group", "metastasized group vs, non-metastasized group", "pre-administered carcinostatic group vs, post-administered carcinostatic group", or "pre-radiation group vs, post-radiation group", etc.

Here, it is assumed that a sample set $X=\{x_1, x_2, \ldots, x_N\}$ and a sample set $Y=\{y_1, y_2, \ldots, y_N\}$ are given. The sample $x_i$ is a numerical vector, where the gene expression level obtained through the micro-array from the biological system of patient i is a component of the vector.

When the number of genes is n, the corresponding patient i can be expressed as an n-dimensional vector. Here, the gene is provided with features, and its attribute to divide as opposing group is, for example, a recurrence group and a non-recurrence group as explained above.

In this manner, the virtual sample set creating section 3 creates the virtual sample sets from the sample sets X15 and Y16 that have been sampled. This method of creating virtual sample sets is widely known as "a sampling with replacement method", "a sampling without replacement method", "a localized linear combination method", and "a noise injection method".

The sampling with replacement method allows restoration to conduct a random retrieval of the samples, and its explanation is omitted here because it is simple.

In the sampling without replacement method, virtual sample sets are created from the sample sets X and Y using the procedure below. A virtual sample set formed with M samples is produced from the sample set X formed with N samples (M<N) by the sampling without replacement. Here, since it is considered that the virtual sample set closely resembles the actual sample set, the value M is set to be as close to the value N as possible. More specifically, it is so set that M=N−1 or N−2. This process is repeated by L times to obtain L virtual sample sets where L is a positive number. Similarly, L virtual sample sets are produced from the sample set Y by the sampling without replacement. By doing so, L pairs of the virtual sample sets are obtained.

In the localized linear combination method, the virtual sample sets are created by the procedure described below. In the localized linear combination method, an influence of the sample to be considered as an outlier can be reduced by localized smoothing.

Procedure 1: Randomly select one sample from the sample set X and denotes it as $x_0$.

Procedure 2: Obtain samples $x_{11}, x_{12}, \ldots, x_{1r}$ that are the closest to $x_0$ (where r is a number).

Procedure 3: Determine the virtual sample x* with use of the following equation (1).

[Expression 1]

$$x^* = \sum_{j=0}^{r} \omega_j x_{ij} \quad (1)$$

Where, $\omega_j$ is a weight which satisfies the equation (2). The value of $\omega_j$ is a random number.

[Expression 2]

$$\sum_{j=0}^{r} \omega_j = 1 \quad (2)$$

Procedure 4: Repeat the Procedures 1 through 3 by N times, thereby producing the virtual sample set of size N.

The virtual sample set is similarly created for the sample set Y as well, and by repeating the above process L times, L pairs of the virtual sample sets can be created.

In the noise injection method, the virtual sample sets are created by the procedure described below. The noise injection method is known as a means to improve a generalization capability in the field of neural network.

Procedure 1: Randomly retrieve one sample x from the sample set X.

Procedure 2: Add noise by the equation (3).

[Expression 3]

$$x^* = x + \epsilon \quad (3)$$

Where $\epsilon$ is an n-dimensional vector which is to be normally distributed according to the expected vector O and covariance matrix I, which is the identity matrix, and is created by a random number.

Procedure 3: Repeat the Procedures 1 through 3 by N times, thereby producing the virtual sample set of size N.

Similar to the localized linear combination method, L pairs of the virtual sample sets are created.

In this manner, various methods can be possible in the creation of the virtual sample sets, and determination as to which method is appropriate depends on a specific problem to be solved, thus, it is practical that a different method should be used for a different problem. The virtual sample set creating section 3 that applies one of the above methods creates the L pairs of the virtual sample sets $(X^1, Y^1), (X^2, Y^2), \ldots (X^L, Y^L)$. In the present invention, the samples included in the virtual sample sets $X^t$ and $Y^t$ that belong to two opposing groups are respectively called virtual samples.

The virtual sample sets $X^t$17 and $Y^t$~created in the manner described in the foregoing are stored in the sample database 14 by the virtual sample set creating section 3.

Next, in the factor selecting section 4 shown in FIG. 1, the following process is conducted for each pair of the virtual sample sets $X^t$17 and $Y^t$18.

Using the pair of virtual sample sets $(X^t, Y^t)$ (t=1, 2, ..., L), an average $\mu_i(X^t)$ and a variance $\sigma_i^2(X^t)$ of the gene expression level of $X^t$ for gene $g_i$ are determined in the statistical quantity operating section 5, and similarly, an average $\mu_i(Y^t)$ and a variance $v_i^2(Y^t)$ of the gene expression level of $Y^t$ are determined. The average value and the variance value of these virtual sample sets are stored in the analysis result database 20 as the virtual sample set average value data 21 and the virtual sample set variance value data 22 by the statistical quantity operating section 5.

Next, the Fisher ratio operating section 6 determines a value of the Fisher ratio $F_i(X^t, Y^t)$ of gene $g_i$ by the equation (4) below. The virtual sample set average value data 21 and the virtual sample set variance value data 22 of the gene expression level can be read out from the analysis result database 20 by the Fisher ratio operating section 6, or the results calculated by the statistical quantity operating section 5 can be directly used as is.

[Expression 4]

$$F_i(X^t, Y^t) = \frac{(\mu_i(X^t) - \mu_i(Y^t))^2}{P_x \sigma_i^2(X^t) + P_y \sigma_i^2(Y^t)} \quad (4)$$

Here, $P_x$ and $P_y$ are a prior probability of X and Y, respectively, and in most cases, $P_x = P_y = \frac{1}{2}$.

The above process is conducted for each gene to determine the Fisher ratio $F_i(X^t, Y^t)$ (t=1, 2, ..., L).

Figure 4:
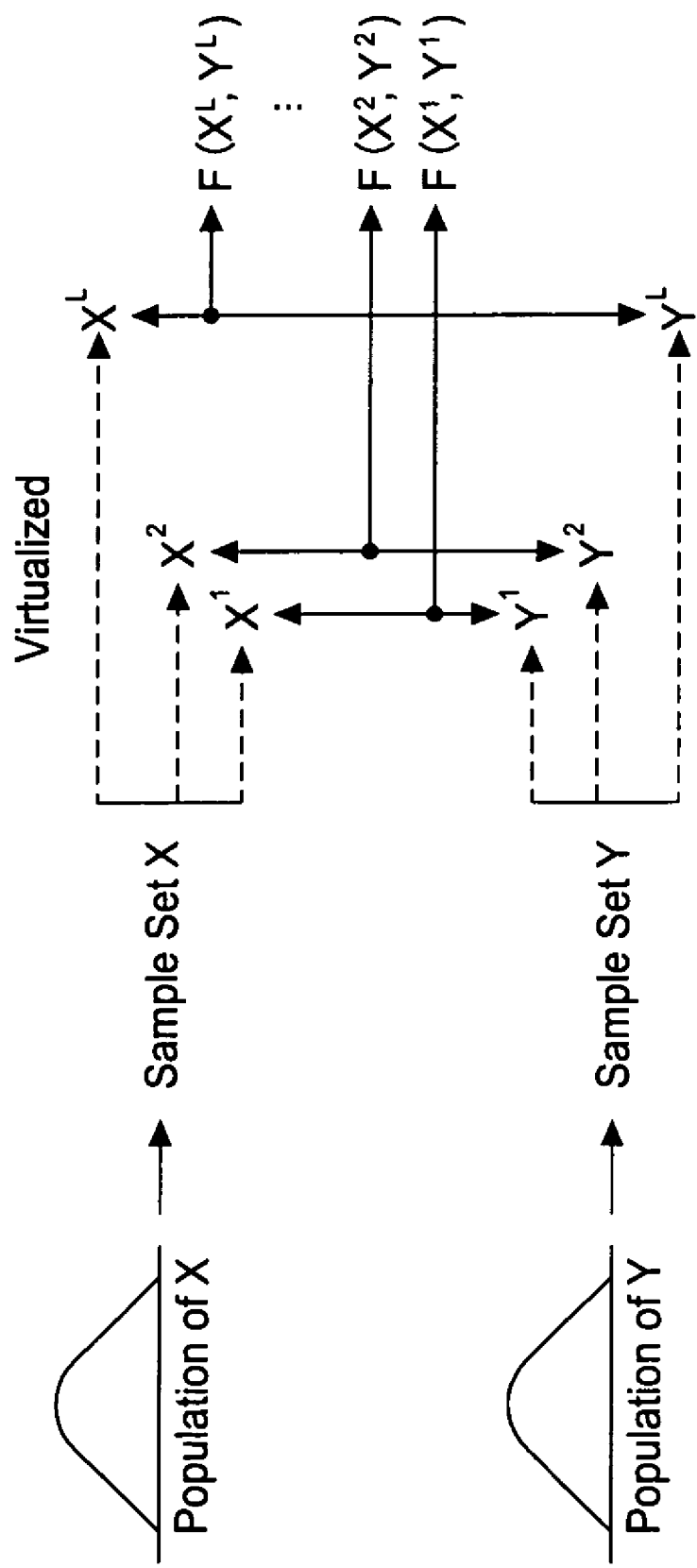
FIG. 4 is a schematic diagram for explaining the operation where the virtual sample sets $X^t$, $Y^t$ are created from sample sets X, Y and the Fisher ratio $F_i(X^t, Y^t)$ is calculated by the effective factor extraction system related to the present embodiment.

FIG. 4 shows this process in a simplified manner. In the effective factor extraction system related to the present embodiment of FIG. 4, the virtual sample sets $X^t$ and $Y^t$ are created from the sample sets X and Y by the virtual sample set creating section, and the Fisher ratio $F_i(X^t, Y^t)$ (t=1, 2, ..., L) for gene i is calculated by the statistical quantity operating section 5 and the Fisher ratio operating section 6.

The Fisher ratio is to distinguish two groups, for example, to evaluate the usefulness of the gene, and it is defined as a normalized average distance with an average spread of the two groups. In other words, the Fisher ratio shows the statistical distance between the two groups. When the value of this Fisher ratio is large, it means that the expression level of the two groups differ greatly. Thus, it becomes possible to select the gene with the larger Fisher ratio.

In the conventional technology, the Fisher ratio is determined by using only one pair of sample sets, where the gene with the larger Fisher ratio value is selected. However, when the sample set that is being used changes, the Fisher ratio value will change as well. For example, with respect to a sample set A, the Fisher ratio value is large so that the gene is recognized as the target cancer gene, however, the Fisher ratio value may become smaller with respect to a sample set B, then the result using the sample set A will be rejected. Therefore, the analysis result is affected strongly by a specific sample set, thereby lacking reliability.

In the present embodiment, however, since L pairs of the virtual sample sets are artificially created per every two groups by the virtual sample set creating section, and the Fisher ratio F, as shown in FIG. 4, is calculated for a plurality of pairs of the virtual sample sets, it is possible to improve the accuracy.

Figure 5:
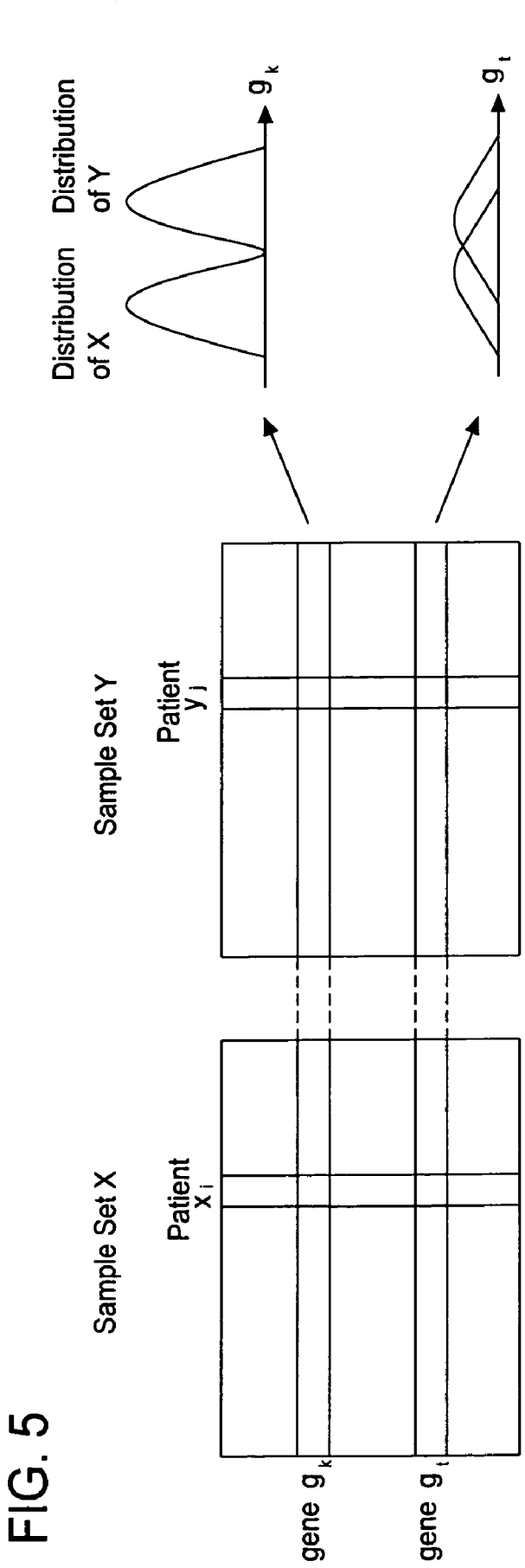
FIG. 5 is a schematic diagram showing the distribution of the feature values (expression levels) of genes in a pair of sample sets.

Here, the attributes of the two groups of the gene will be explained with reference to FIG. 5, and the concept of large or small Fisher ratio will be explained with reference to FIGS. 6 and 7. FIG. 5 is a schematic diagram showing the distribution of the feature value (expression level) of the gene in a pair of sample sets, and FIG. 6 is a schematic diagram showing the distribution of the expression level (mRNA) in the coordinates for the genes $g_k$, $g_t$ related to 5 pairs of sample sets.

In FIG. 5, the sample sets X and Y are constructed by the gene information of patients, and the attributes of each of the sample sets are represented by, for example, X vs. Y, such as cancer vs. non-cancer. When the distribution of the feature value in each of the sample sets is focused on the two genes $g_k$ and $g_t$, the distribution of $g_k$ is more clearly separated, thus, it is considered that $g_k$ rather than $g_t$ is more effective for distinguishing two groups. In other words, $g_k$ is more appropriate for the target gene.

When such sample sets are created, the effective factor extraction system of the present embodiment establishes virtual sample sets from the sample sets, and by calculating the statistical quantity as described above using the virtual sample sets to obtain the Fisher ratio expressed in equation (4), the extent of separation of the distribution of the genes shown in FIG. 5 can be evaluated to determine the target gene.

Figure 6:
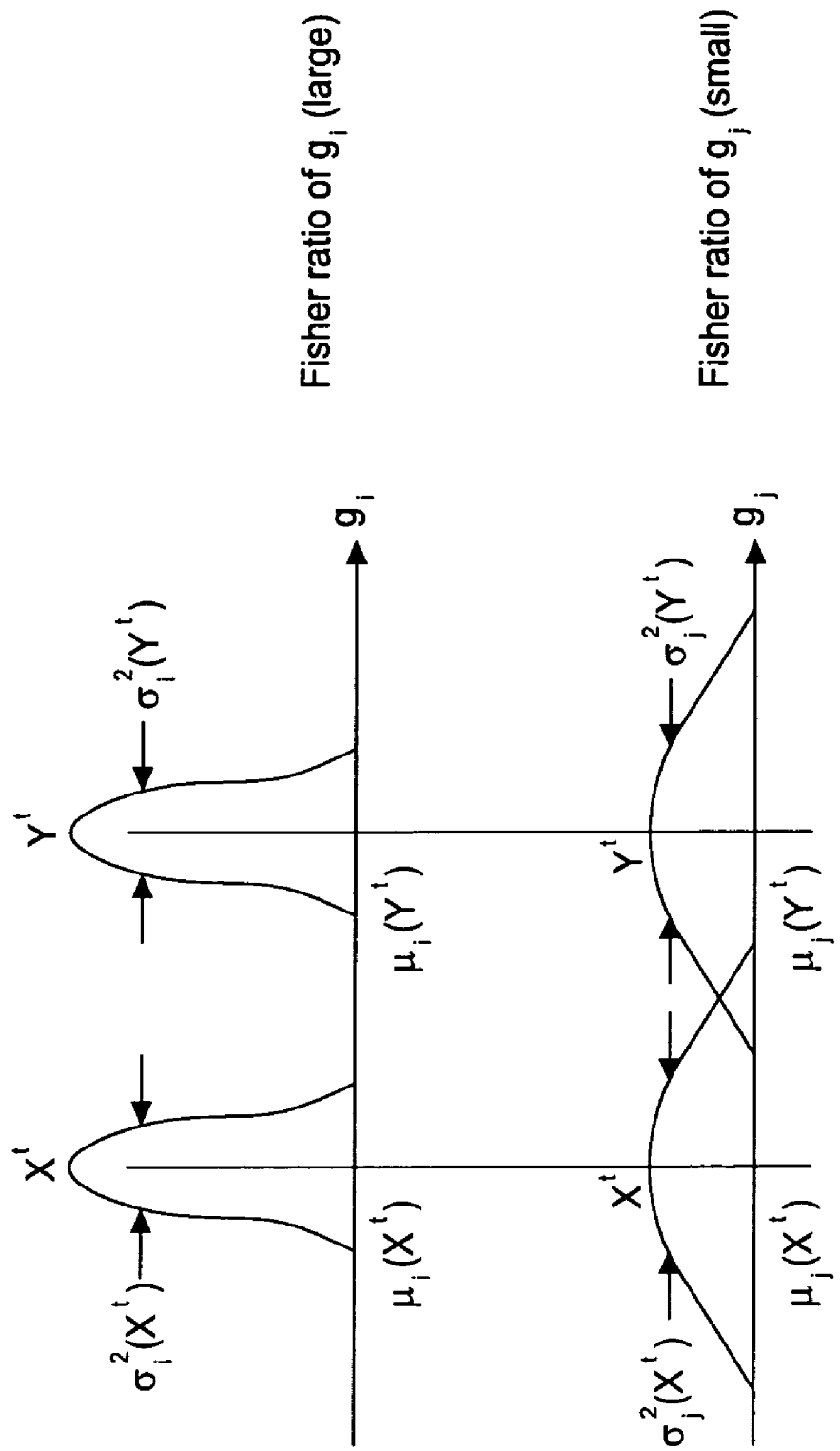
FIG. 6 is a schematic diagram for applying a distribution diagram of the virtual sample sets shown in FIG. 5 and for explaining the degree of the Fisher ratio by further adding the statistical amounts such as average values and variance values.
Figure 7:
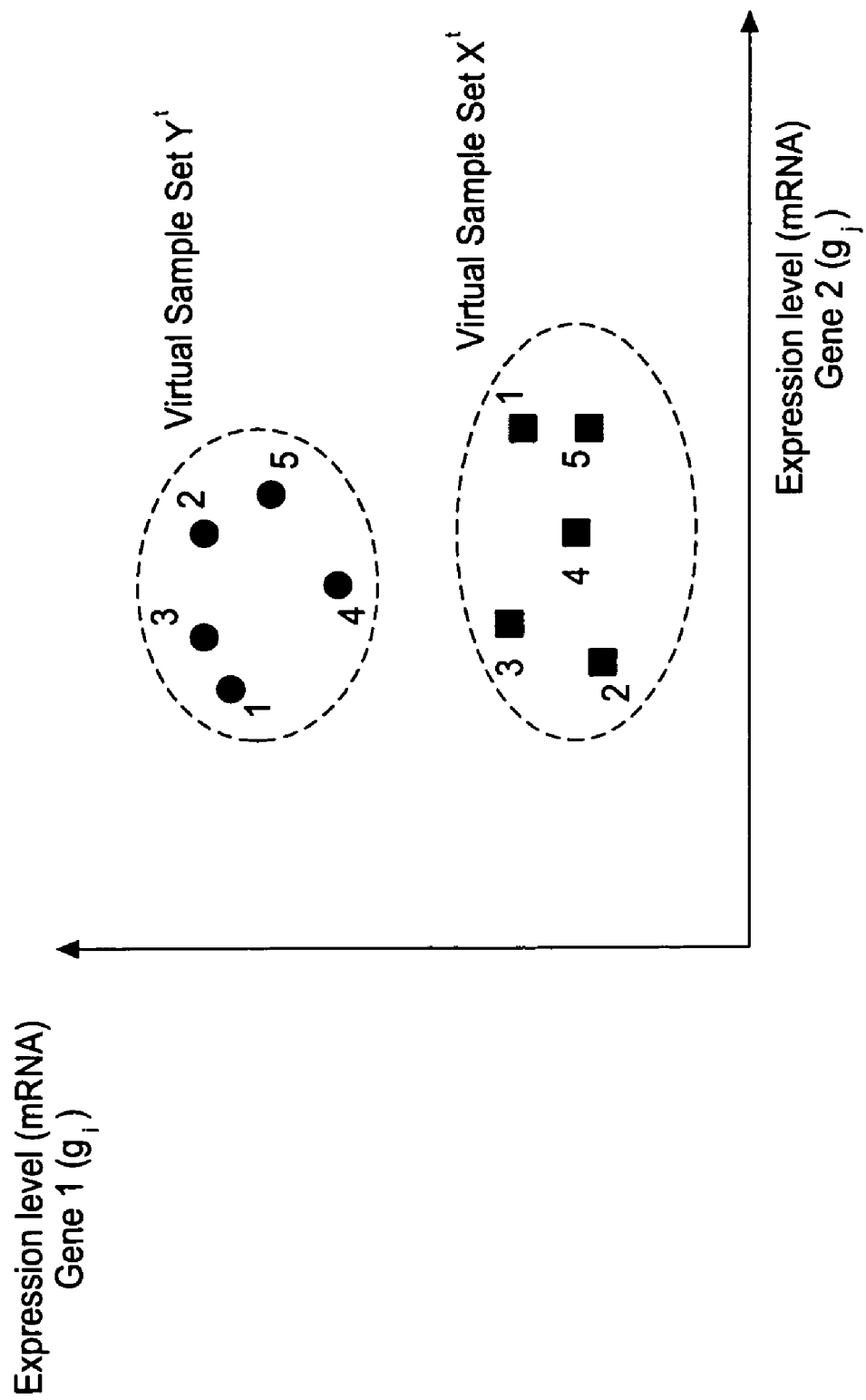
FIG. 7 is a schematic diagram for explaining the degree of the Fisher ratio by assigning the expression levels (mRNA) of the two genes $g_i$, $g_j$ to the y axis and the x axis, respectively.

FIG. 6 applies the distribution diagram of FIG. 5 to the virtual sample sets and further incorporates the statistical quantity such as the average value data and variance value data.

When the distribution of the virtual sample sets $X^t$ and $Y^t$ with respect to the feature value (expression level) of the two genes $g_i$ and $g_j$ is examined, it is understood that the gene $g_i$ is clearly separated between the sample sets $X^t$ and $Y^t$, however, the distributions on the gene $g_j$ are overlapped and cannot be separated. In such a case, the Fisher ratio is large for $g_i$ and is small for $g_j$. In such two genes, as mentioned above, it is understood that the target gene thought to be effective for separating the virtual sample sets $X^t$ and $Y^t$ is $g_i$.

This will be more specifically explained with reference to FIG. 7. FIG. 7 shows the expression level (mRNA) of the two genes $g_i$ and $g_j$ in the y-axis and x-axis, respectively. The numerals indicate the sample numbers. In this diagram, the gene expression levels of patients included in the sample set Y represented by the circle marks are almost the same as the gene expression levels included in the sample set X represented by the square marks for gene $2(g_j)$. However, the gene expression levels of patients included in the virtual sample set $Y^t$ represented by the circle marks clearly show greater values than the gene expression levels of patients included in the virtual sample set $X^t$ represented by the square marks for gene $1(g_i)$, thus, it is understood that the target gene is $g_i$.

As an indicator for clarifying the difference between such gene expression levels, the Fisher ratio shown by the equation (4) is calculated by the Fisher ratio operating section 6. The calculated Fisher ratio is stored as the Fisher ratio data 23 in the analysis result database 20 by the Fisher ratio operating section 6.

The sorting section 7 reads out the Fisher ratio data 23 stored in the analysis result database 20 or directly utilizes the Fisher ratio data calculated by the Fisher ratio operating section 6 to rank the factors, i.e., the genes in a descending order based on the amount of the Fisher ratio value.

Among the genes that are ranked in the descending order, the gene of higher rank, the greater the Fisher ratio, i.e., the target gene which is appropriate for clearly separating the two groups. The Fisher ratio data 23 ranked in such a manner can be stored in the analysis result database 20 by the sorting section 7, or directly transferred to the testing section 8 as is without being stored. The ranking by the sorting section 7 does not always have to be in the descending order, and can be in an ascending order as well.

Using the ranked Fisher ratio data 23, the testing section 8 determines a significance level by, for example, a random permutation test method, and conducts a statistical test to determine a number of effective genes for distinguishing the two groups. In other words, it determines how many genes are appropriate as target genes that are capable of distinguishing the two groups.

In the random permutation test method, by rejecting a null hypothesis which assumes that the two groups are equal, the effective genes for distinguishing the two groups can be determined. Here, it is assumed that there is a sample set X and a sample set Y from the two groups to be distinguished. First, the two groups are assumed to be equal, and the samples from a mixed sample set which combines the sample set X and the sample set Y are randomly retrieved to create a pseudo sample set X and a pseudo sample set Y. The Fisher ratio for each gene is calculated with respect to the pseudo sample sets X and Y. The process for creating the pseudo sample sets X and Y and calculating the Fisher ratio of each gene is independently repeated, for example, 1000 times to determine the distribution of the Fisher ratios. An upper limit of the distribution of the Fisher ratios is determined by a threshold value α based on a certain significance level. The number of repeating the processes can be properly set each time so as to obtain an intended reliability of the results, or such a number can be stored in the sample database 14 from the input section 1 as analysis constant data 19. The threshold value α is treated in the same manner.

Here, the proposition "if the two groups are equal, then all possible Fisher ratio values are less than the threshold value α" is considered, and if the contraposition of this proposition is taken, then it can be said that "if the Fisher ratio values are greater than the threshold value α, then the two groups are different." Thus, the genes having the Fisher ratios that are greater than the threshold value α are considered as the effective genes for distinguishing the two groups. Generally, genes and their numbers that are effective in each virtual sample set are different, and each gene subset is statistically effective only for the virtual sample set used in the Fisher ratio calculation.

When such a test is executed for L pairs of virtual sample sets, L gene subsets determined to be effective for the L pairs of the virtual sample sets can be obtained.

In the present embodiment, the random permutation test method is used as a test method, however, the present invention is not limited to this particular method, and any other methods can be used as long as it is capable of distinguishing the two groups with respect to the amounts of the Fisher ratios.

The testing section 8 stores the test result with respect to the L pairs of virtual sample sets, i.e., the Fisher ratios as well as the gene sets that are appropriate as target genes that have established these Fisher ratios, which distinguish the two groups, in the analysis result database 20 as tested result data 25.

The frequency analyzing section 9 reads out the tested result data 25 from the analysis result database 20 or directly uses the tested result data 25 obtained by the testing section 8 and selects the genes that are included in all of the gene subsets, namely, the genes that are determined to be effective in any virtual sample set.

Then, these genes are recognized as the target genes with greater precision. Alternatively, these conditions can be softened so that the genes that are, for example, 80% or 70% effective are recognized as the target genes.

Figure 8:
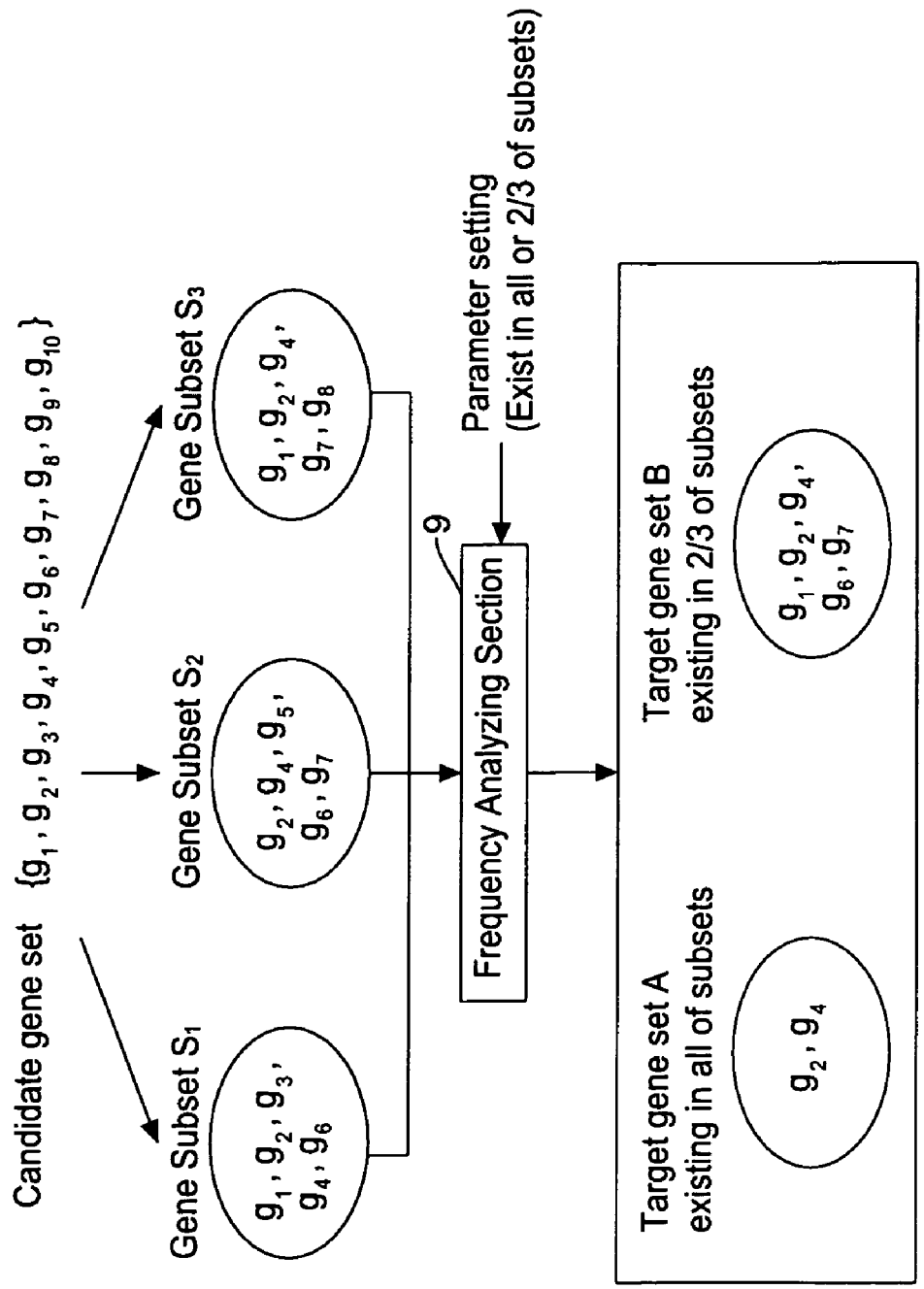
FIG. 8 is a schematic diagram for explaining the function of the frequency analyzing section of the effective factor extraction system related to the present embodiment.

The method of determining the target gene by the frequency analyzing section 9, namely, the method of determining the target factor will be explained in detail with reference to FIG. 8. In FIG. 8, when candidate genes are denoted by $g_1$~$g_{10}$, it is assumed that respective gene subsets $S_1$, $S_2$, $S_3$ are created with respect to virtual sample sets 1, 2, and 3 by the testing section 8. As shown in the drawing, the genes that are the candidates are included per every virtual sample set, however, they do not always and completely match with one another.

Therefore, with use of the frequency analyzing section 9, the analysis conditions are pre-set as, for example, those that appear in all of the gene subsets or two out of three gene subsets. This setting is preferably input by the input section 1 as the analysis condition 13 and is stored in the sample database 14 as the analysis constant data 19. The analysis conditions can be properly set by the user, and is not limited to particular numerical values such as all or ⅔. Also, several analysis conditions can be used at the same time, where, as shown in FIG. 8, the result is represented for every analysis condition.

According to FIG. 8, in the case where the condition is so set that candidate genes appear in all of the gene subsets, the genes $g_2$ and $g_4$ are selected as the target genes, and in the case where they appear in two out of three gene subsets, genes $g_1$, $g_6$, and $g_7$ are additionally selected thereto to create a target gene set B.

The target gene set is obtained in this manner. The data related to the target gene set obtained in this manner is stored in the analysis result database 20 as factor extraction data 26 by the frequency analyzing section 9.

Next, in the generalized Fisher ratio operating section 10, a generalized Fisher ratio is calculated for each gene in the target gene set obtained by the frequency analyzing section 9. The data related to this target gene set can be directly retrieved from the frequency analyzing section 9, or retrieved as the factor extraction data 26 from the analysis result database 20.

Prior to the calculation by the generalized Fisher ratio operating section 10, first, an average $\mu(F_i)$ and a variance $\sigma^2(F_i)$ of the Fisher ratio $F_i$ shown in the respective equations (5) and (6) are calculated. This average value and variance value can be stored in the analysis result database 20 as the virtual sample set average value data 21 and the virtual sample set variance data 22, or can be read out as is from the generalized Fisher ratio operating section 10.

[Expression 5]

$$\mu(F_i) = \frac{1}{R}\sum_{t=1}^{R} F_i(X^t, Y^t) \qquad (5)$$

$$\sigma^2(F_i) = \frac{1}{R-1}\sum_{t=1}^{R} \{F_i(X^t, Y^t) - \mu(F_i)\}^2 \qquad (6)$$

Here, R denotes the number of genes within the target gene set. Next, the generalized Fisher ratio operating section 10 reads out $\mu(F_i)$ and $\sigma^2(F_i)$ from the statistical quantity operating section 5 or the analysis result database 20 to calculate the generalized Fisher ratio such as a one expressed by the equation 7 shown below.

[Expression 6]

$$F_i^* = \frac{H(\mu(F_i))}{G(\sigma^2(F_i))} \qquad (7)$$

Here, $H(\mu(F_i))$ is the function of $\mu(F_i)$, and the larger the value of the numerator $H(\mu(F_i))$, the larger the difference is between two groups. On the other hand, the denominator $G(\sigma^2(F))$ is the function of $\sigma^2(F_i)$ and indicates the fluctuation amount (positive value) of the Fisher ratios in accordance with differing samples, where the smaller this value is, the greater the reliability of the analysis results. Because of the foregoing, the gene with a larger ratio between $H(\mu(F_i))$ and $G(\sigma^2(F))$ means that it is a gene having a smaller value of $G(\sigma^2(F))$ and a larger value of $H(\mu(F_i))$.

In this situation, this gene has a high reliability and a large difference of the expression level in average from any virtual sample set. The critical difference between the technology using the generalized Fisher ratio and the other technology is that the Fisher ratio is treated as a random variable instead of a fixed value as is used in the other technology.

The detailed example of the generalized Fisher ratio is shown by the following equations (8)~(10), although the present invention is not limited to these equations. For example, the parameter α of equation (10) can be input in advance via the input section 1 as the analysis constant data 19 and stored in the sample database 14.

[Expression 7]

$$F_i^*(1) = \frac{\mu(F_i)}{\sigma^2(F_i)} \tag{8}$$

$$F_i^*(2) = \frac{\mu(F_i)}{\log_{10} \sigma^2(F_i)} \tag{9}$$

$$F_i^*(3) = \frac{\mu(F_i)}{\sigma^2(F_i) + \alpha} \quad \alpha \text{ is a parameter} \tag{10}$$

The generalized Fisher ratio calculated by the generalized Fisher ratio operating section 10 is stored in the analysis result database 20 as the generalized Fisher ratio data 24 by the generalized Fisher ratio operating section 10.

In the sorting section 7, the target genes are ranked based on the values of the generalized Fisher ratio in the descending order. The data used during this process can be directly read out from the generalized Fisher ratio operating section 10, or read out from the analysis result database 20 as the generalized Fisher ratio data 24.

The target genes that have been ranked in the descending order are basically shown so that the medical and biological target genes can be selected from the top thereof, however, the final selection of the target gene will be modified by a judgment made by a user who is operating the present effective factor extraction system of the present invention since the effective factor extraction system is a support system for easily making the final judgment.

The output section 11 displays/outputs the data and analysis conditions to be applied to the operating section 2 and to the sample database 14 through the input section 1, and by using these data, it outputs the input data and analysis conditions selected for the operation by the virtual sample set creating section 3 and the factor selecting section 4 as well as the calculation results thereof. Naturally, it is also possible for the output section 11 to display/output the finally selected factor, and the target gene in accordance with the present embodiment.

The relationship between the flow of analysis explained above and the structure of the effective factor extraction system of the present invention will be more clearly described with reference to FIG. 9.

Figure 9:
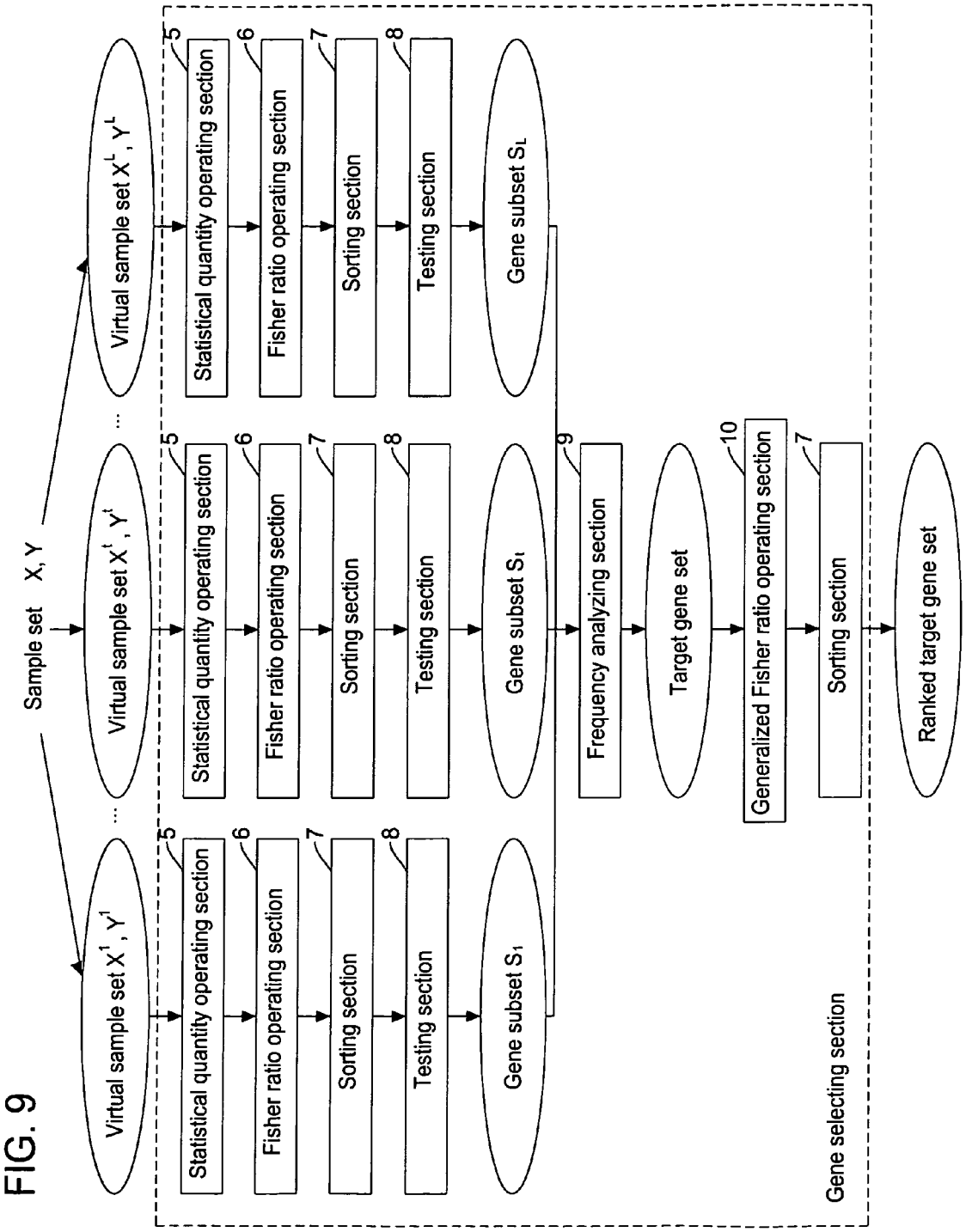
FIG. 9 is a schematic diagram for explaining the analysis flow of the effective factor extraction system related to the present embodiment.

Referring to FIG. 9, it is easily understood that there are sample sets X and Y, and from these sample sets, L pairs of the virtual sample sets are created with use of the virtual sample set creating section 3, where L gene subsets $(S_1, \ldots S_l, \ldots, S_L)$, which are subsets of the genes, are selected with use of the factor selecting section 4 with respect to each of the virtual sample sets.

Based on the virtual sample sets, by calculating the Fisher ratio and executing the test, target genes with a certain level of high accuracy can be obtained at this stage.

However, in order to pursue higher accuracy, by using these gene subsets, the frequency analysis section 9 selects the genes in each subset, and the generalized Fisher ratio operating section 10 calculates the generalized Fisher ratio. As previously explained, by obtaining the Fisher ratio as the random variable in each gene subset, calculating the generalized Fisher ratio for the entire virtual sample sets, and ranking them by the sorting section 7, a target gene that has a higher reliability than the target gene for a particular gene subset can be extracted.

Next, an embodiment for actually calculating the Fisher ratio with use of the virtual sample sets $X^t$ and $Y^t$ will be explained.

In FIG. 10, virtual sample sets are created from the sample sets of opposing groups, a recurrence group and a non-recurrence group, by the virtual sample set creating section 3. Based on the virtual sample sets created in this manner, a virtual sample set $X^t$ (recurrence group) and a virtual sample set $Y^t$ (non-recurrence group) are selected as an example. Each of the virtual sample sets $X^t$ and $Y^t$ includes three patients $(x_1, x_2, x_3)$ and $(y_1, y_2, y_3)$, and the gene expression levels of genes $\sigma_1 \sim \sigma_5$ out of a large number of genes are shown in the table of FIG. 10. The gene expression level is defined as the mRNA amount as previously explained.

Using the data of FIG. 10 that has been collected in this manner, averages $\mu_1, \mu_2$ and variances $\sigma_1, \sigma_2$ are calculated by the statistical quantity operating section 5 for every gene for each of the virtual sample sets, and based on these averages and variances, the Fisher ratio as shown by the equation (4) is calculated by the Fisher ratio operating section 6. The results of the calculation are shown in FIG. 11 with respect to each gene. A priori probability is ½ for each calculation of the Fisher ratio.

According to FIG. 11, it is apparent that among the genes $g_1 \sim g_5$, the gene $g_3$ has the largest Fisher ratio and thus it is the most favorable as a target gene.

From the condition shown in the table of FIG. 11, the sorting section 7 ranks the Fisher ratios in a descending order or an ascending order, and the testing section 8 determines the significance level, conducts the statistical test, and determines a number of genes effective for distinguishing the two groups.

After that, by the frequency analyzing section 9, as explained above with reference to FIG. 8, a frequency analysis is conducted with respect to the gene subsets extracted by the testing section 8 for each virtual sample set to create a target gene set. Then, the generalized Fisher ratio is calculated by the generalized Fisher ratio operating section 10 to select and extract the target genes with high accuracy.

Next, the effective factor extraction method and the effective factor extraction program related to the preferred embodiment of the present invention will be explained. The effective factor extraction system has been explained in the foregoing, and this invention can also be contemplated as a method invention or a program for executing the computer.

Since the matters that have been explained with respect to the embodiment of the effective factor extraction system can be substantially the same in the embodiment of the method invention or the program invention, the explanation of each of data and sample sets will be abbreviated. Referring to FIG. 9, for example, there are sample sets X and Y. Here, the process for creating L pairs of the virtual sample sets (where L is a number) based on the sample sets is hereafter referred to as a virtual sample set creating process, and the process for reading out the parameter amounts reserved by the virtual samples in the virtual sample sets per every factor such as a gene and calculating the average value and variance for every group is hereafter referred to as a statistical quantity operating process.

Further, the process for calculating the Fisher ratio for each gene, which is the factor, as the statistical distance between the groups based on the average value and variance calculated for each group is hereafter referred to as a statistical distance operating process, and using the statistical distance of the Fisher ratio calculated for each gene, the process for testing significant genes for distinguishing the two groups is hereafter referred to as a testing process.

Namely, the functions exerted by the virtual sample set creating section 3, the statistical quantity operating section 5, the Fisher ratio operating section 6, and the testing section 8 are interpreted as processes in terms of time, where the effective factor extraction method connects these processes and the effective factor extraction program executes these processes on the computer.

On the computer, the system structure as shown in FIG. 1 can be constructed as is. For example, the input section 1 is conceptualized as a keyboard or other input device of the computer, and the output section 11 is conceptualized as a display such as a CRT and a liquid crystal display, or the interface between another system. The sample database 14 and analysis result database 20 are also conceptualized as a storage medium such as a hard disk or a memory for storing the respective data.

The operating section 2 corresponds to the center processing unit (CPU) of the computer. The virtual sample set creating section 3 in the operating section 2, the statistical quantity operating section 5 for constructing the factor selecting section 4, the Fisher ratio operating section 6, the sorting section 7, the testing section 8, the frequency analyzing section 9, and the generalized Fisher ratio operating section 10 are elements in the computer constituted by the CPU, and moreover, the functions exerted by each of the elements can be conceptualized as the process attained in terms of time. Executing these processes in the computer is the program.

More specifically, the explanations made for the system above can be equally applied to the method and program. For example, the sample set X15 and the sample set Y16 entered via the input section 1 and stored in the sample database 14 are read out by the virtual sample set creating section 3. The virtual sample set creating section 3 creates a plurality of virtual sample sets $X^t$ and $Y^t$. Such series of functions are achieved by the execution of the program. Alternatively, the processes attained in terms of time that achieve such functions are executed. When the contents explained with respect to the effective factor extraction system are attained by the computer in the same manner, the respective elements assumed in the CPU are attained by the execution of the necessary program for exerting the functions.

In such an effective factor extraction method and program, the same operations and effects as that in the effective factor extraction system can be achieved, however, the target gene extraction of higher accuracy can be examined, where like the effective factor extraction system, by methods and programs of other embodiments.

Namely, the significant factors (genes) can be extracted in the testing process, however, if the set of the selected genes, as shown in FIG. 9, are listed as the gene subsets S, the frequency analyzing process is established as a process for extracting the genes existing with higher frequency than the predetermined frequency, and the generalized statistical distance operating process is established as a process for calculating the generalized Fisher ratio from the average values and variance values of the statistical distance such as the Fisher ratio for each of the target gene sets extracted in the frequency analyzing process.

Then, the sorting process for ranking the generalized statistical distances such as the generalized Fisher ratios in either the descending or ascending order, and the display process for displaying the contents of the ranked target gene set, the generalized statistical distances such as the generalized Fisher ratios, the calculated results and the conditions used, and the data, which have been obtained by the sorting process, can be established.

Since the effective factor extraction method and the program that executes the processes in the computer are established with such processes, it is possible to attain the operations and effects of the system described above.

Particularly, in such an effective factor extraction program, the system structure as shown in FIG. 1 can be obtained as a structure established by the computer as explained above. The explanation of the prior embodiment of the effective factor extraction program can be equally applied to the present embodiment of the effective factor extraction program.

What is claimed is:

1. A method of extracting factors that distinguish between two groups, comprising:
   (a) receiving, from a sample database stored in a storage medium, a set of samples, wherein each sample comprises a set of factors having quantitative values, and wherein each sample belongs to one of two groups (X and Y);
   (b) creating, using a CPU, a first virtual sample set ($X^t$) by randomly sampling the set of samples belonging to the first group;
   (c) creating, using the CPU, a second virtual sample set ($Y^t$) by randomly sampling the set of samples belonging to the second group;
   (d) calculating the mean ($\mu_i(X^t)$) and variance $$(\sigma_i^2(X^t))$$

of the quantitative values for each factor of the samples in the first virtual sample set;
   (e) calculating the mean ($\mu_i(Y^t)$) and variance $$(\sigma_i^2(Y^t))$$

of the quantitative values for each factor of the samples in the second virtual sample set;
   (f) calculating, using the CPU, the Fisher ratio $$\left(F_i(X^t, Y^t) = \frac{(\mu_i(X^t) - \mu_i(Y^t))^2}{P_x \sigma_i^2(X^t) + P_y \sigma_i^2(Y^t)}\right)$$

of each factor, wherein $P_x$ and $P_y$ are the prior probabilities of a sample belonging to X or Y, respectively;
   (g) using the Fisher ratios to identify factors that are effective to distinguish the two groups;
   (h) combining the identified factors and their corresponding Fisher ratios ($F_i$) into a factor subset;
   (i) repeating steps (b)-(h), thereby generating a plurality of factor subsets;
   (j) determining the frequency of each factor in the plurality of factor subsets;
   (k) extracting the factors having a frequency that exceeds a chosen threshold;
   (l) combining the extracted factors, and a set ($F_i$) of the Fisher ratios corresponding to each extracted factor, into a target factor set;
   (m) calculating the mean ($\mu(F_i)$) and variance ($\sigma^2(F_i)$) of the set of Fisher ratios of each factor in the target factor set;

(n) calculating, using the CPU, a generalized Fisher ratio $$(F_i^*)$$

of each factor in the target factor set using the function $$F_i^* = \frac{H(\mu(F_i))}{G(\sigma^2(F_i))},$$

wherein H(•) and G(•) are functions;
(o) ranking the factors in the target factor set according to their generalized Fisher ratios; and
(p) storing the ranked target factor set in an analysis result database in the storage medium.

2. The method of claim 1, wherein the factor is a gene and the quantitative value is a measurement of mRNA expression.

3. The method of claim 1, wherein H(•) and G(•) are the identity function.

4. The method of claim 1, wherein H(•) is the identity function and G(•) is $\log_{10}$(•).

5. The method of claim 1, wherein H(•) is the identity function and $G(\sigma^2(F_i)) = \sigma^2(F_i) + \alpha$, wherein $\alpha$ is a parameter.

6. A system for extracting factors that distinguish between two groups, comprising a CPU, a database storage medium, and a computer program that causes the CPU to perform the following operations:
(a) receiving, from a sample database stored in the storage medium, a set of samples, wherein each sample comprises a set of factors having quantitative values, and wherein each sample belongs to one of two groups (X and Y);
(b) creating a first virtual sample set ($X^t$) by randomly sampling the set of samples belonging to the first group;
(c) creating a second virtual sample set ($Y^t$) by randomly sampling the set of samples belonging to the second group;
(d) calculating the mean ($\mu_i(X^t)$) and variance $$(\sigma_i^2(X^t))$$

of the quantitative values for each factor of the samples in the first virtual sample set;

(e) calculating the mean ($\mu_i(Y^t)$) and variance $$(\sigma_i^2(Y^t))$$

of the quantitative values for each factor of the samples in the second virtual sample set;
(f) calculating the Fisher ratio $$\left(F_i(X^t, Y^t) = \frac{(\mu_i(X^t) - \mu_i(Y^t))^2}{P_x \sigma_i^2(X^t) + P_y \sigma_i^2(Y^t)}\right)$$

of each factor, wherein $P_x$ and $P_y$ are the prior probabilities of a sample belonging to X or Y, respectively;
(g) using the Fisher ratios to identify factors that are effective to distinguish the two groups;
(h) combining the identified factors and their corresponding Fisher ratios ($F_i$) into a factor subset;
(i) repeating steps (b)-(h), thereby generating a plurality of factor subsets;
(j) determining the frequency of each factor in the plurality of factor subsets;
(k) extracting the factors having a frequency that exceeds a chosen threshold;
(l) combining the extracted factors, and a set ($F_i$) of the Fisher ratios corresponding to each extracted factor, into a target factor set;
(m) calculating the mean ($\mu(F_i)$) and variance ($\sigma^2(F_i)$) of the set of Fisher ratios of each factor in the target factor set;
(n) calculating, using the CPU, a generalized Fisher ratio ($F'_i$) of each factor in the target factor set using the function $$F_i^* = \frac{H(\mu(F_i))}{G(\sigma^2(F_i))},$$

wherein H(•) and G(•) are functions;
(o) ranking the factors in the target factor set according to their generalized Fisher ratios; and
(p) storing the ranked target factor set in an analysis result database in the storage medium.

* * * * *